(12) United States Patent
Naciri et al.

(10) Patent No.: US 9,201,010 B2
(45) Date of Patent: Dec. 1, 2015

(54) FLUORESCENT ORGANIC NANOPARTICLES

(75) Inventors: Jawad Naciri, Herndon, VA (US); Christopher M Spillmann, Alexandria, VA (US); George P Anderson, Bowie, MD (US); Banahalli R Ratna, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 908 days.

(21) Appl. No.: 12/431,784

(22) Filed: Apr. 29, 2009

(65) Prior Publication Data

US 2009/0272913 A1     Nov. 5, 2009

Related U.S. Application Data

(60) Provisional application No. 61/049,446, filed on May 1, 2008.

(51) Int. Cl.
   G01N 21/64     (2006.01)
   C09K 11/02     (2006.01)
   (Continued)

(52) U.S. Cl.
   CPC ............ *G01N 21/6428* (2013.01); *B82Y 20/00* (2013.01); *B82Y 30/00* (2013.01);
   (Continued)

(58) Field of Classification Search
   USPC .................................. 349/156; 428/403–405
   See application file for complete search history.

(56) References Cited

U.S. PATENT DOCUMENTS

| 5,151,516 A | 9/1992 | Beck et al. |
| 5,891,738 A * | 4/1999 | Soini et al. ................. 436/501 |

(Continued)

FOREIGN PATENT DOCUMENTS

JP     2000345160 A  * 12/2000

OTHER PUBLICATIONS

Balakrishnan et al. (Effect of Side-Chain Substituents on Self-Assembly of Perylene Diimide Molecules: Morphology Control, J. Am. Chem. Soc. 2006, 128, 7390-7398).*

(Continued)

*Primary Examiner* — Alexandre Ferre
(74) *Attorney, Agent, or Firm* — US Naval Research Laboratory; Joseph T. Grunkemeyer

(57) ABSTRACT

A nanoparticle having a surfactant shell with a hydrophilic outer surface and a hydrophobic inner surface and an organic chromophore and a polymer having aromatic groups within the surfactant shell. A method of making nanoparticles by: emulsifying an aqueous composition of a surfactant and an organic solution of a monomer and an organic chromophore to form micelles of the monomer and the chromophore inside a surfactant shell; and polymerizing the monomer. A method of: reacting a ω-bromoalkyl acid with acryloyl acid lithium salt, and reacting the product with sodium hydride to produce an acryloyloxyalkyl carboxylic acid sodium salt. The compound shown below.

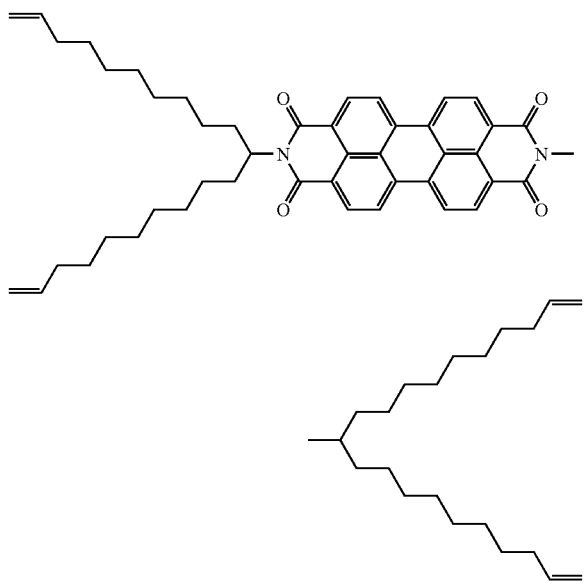

15 Claims, 11 Drawing Sheets

(51) Int. Cl.

| | | |
|---|---|---|
| C07D 471/06 | (2006.01) | |
| B82Y 20/00 | (2011.01) | |
| B82Y 30/00 | (2011.01) | |
| C09K 11/06 | (2006.01) | |
| H05B 33/14 | (2006.01) | |

(52) U.S. Cl.
CPC ............ *C07D 471/06* (2013.01); *C09K 11/06* (2013.01); *H05B 33/14* (2013.01); *C09K 2211/1416* (2013.01); *C09K 2211/1433* (2013.01); *C09K 2211/1466* (2013.01); *G01N 2021/6439* (2013.01); *G01N 2021/6441* (2013.01)

(56) References Cited

U.S. PATENT DOCUMENTS

| | | |
|---|---|---|
| 7,176,255 B2 | 2/2007 | Mathauer et al. |
| 2005/0176029 A1 | 8/2005 | Heller et al. |
| 2007/0013829 A1 | 1/2007 | Stephenson et al. |
| 2007/0228326 A1 | 10/2007 | Goldfinger et al. |
| 2008/0095699 A1 | 4/2008 | Zheng et al. |

OTHER PUBLICATIONS

Kawai et al. (Anisotropic Translational Diffusion of Single Fluorescent Perylene Molecules in a Nematic Liquid Crystal, ChemPhysChem 2004, 5, 1606-1609).*
Tichagwa et al. (The use of Selected Acrylate and Acrylamide-Based Surfmers and Polysoaps in the Emulsion Polymerization of Styrene, Macomol. Symp. 193, 251-260 (2003)).*
Guyot et al. (Advances in Reactive surfactants, Advances in Colloid and Interface Science. 108-109. (2004) 3-22).*
Thiem et al. (Photopolymerization of Reactive Mesogens, Macromol. Chem and Phys., 2005, 206, 2153-2159).*
Machine translation of Komatsu et al. (JP 2000-345160 A).*
Zhang et al. (Synthesis and Fluorescence Quenching of Copolymer Containing 3,4,9,10-Perylenetetracarboxyl Diimide Side Chains, Chinese Chemical Letters vol. 10, No. 11, pp. 953-956, 1.*
Murcia et al. (Biofunctionalization of Fluorescent Nanoparticles, Nanotechnologies for the Life Sciences vol. 1, Wiley-VCH, 2005).*
Ho et al. (Liquid crystal dyes with high solubility and large dielectric anisotropy, Appl. Phys. Lett. 64 (17), 1994).*
Herz et al. (Effects of aggregation on the excitation transfer in perylene-end-capped polyindenofluorene studied by time-resolved photoluminescenceroscropy, Phys. Rev. B., vol. 64, 2001, 195203).*
Wang et al. (Dynamic pi-pi Stacked Molecular Assemblies Emit from Green to Red Colors, Nano Lett. vol. 3, No. 4. pp. 455-458 (2003)).*
Landfester, "Miniemulsions for Nanoparticle Synthesis" Top. Curr. Chem., (2003) 227: 75-123.
Langhals et al., "The Relation between Packing Effects and Solid State Fluoresence of Dyes" J. Prakt. Chem., 333, 733, (1991).
Spillman et al., "Role of Surfactant in the Stability of Liquid Crystal-Based Nanocolloids" Langmuir 2009, 25, 2419-2426.
Vennes et al., "Smectic Liquid-Crystalline Colloids by Miniemulsion Techniques" Adv. Mater. 2005, 17, 2123-2127.
PCT Search Report and Written Opinion in PCT/US09/42009.

* cited by examiner

FLUORESCENT ORGANIC NANOPARTICLES

The application claims the benefit of U.S. Provisional Patent Application No. 61/049,446, filed on May 1, 2008. The provisional application and all other patent documents and publications referred to throughout this nonprovisional application are incorporated herein by reference.

TECHNICAL FIELD

The disclosure is generally related to fluorescent nanoparticles.

DESCRIPTION OF RELATED ART

Over the last several decades, studies on liquid crystals (LCs) have gained a lot of impetus due to its impact on the flat panel display technology. However, the advantage of the inherent spontaneous molecular order in these materials is also being taken advantage of for developing non-display applications of liquid crystals. Supra molecular ordered assemblies such as liquid crystals provide an excellent framework for incorporating anisotropy in materials. One area of technology with vast potential is the inclusion of anisotropy in nanovolumes. In particular, taking advantage of the spontaneous ordering of liquid crystalline molecules to produce isotropically-shaped nanoparticles with anisotropic material properties.

Polymeric nanospheres are a class of materials used for a wide range of applications from controlled release to photonics. Though monodisperse particles have been developed and used to create highly organized lattice structures, the particles themselves are composed of randomly coiled polymer chains, thus rendering them isotropic and passive materials. Liquid crystal nanocolloids have been prepared using a well-established miniemulsion technique (Landfester, *Top. Curr. Chem.* 227, 75, (2003)).

Organic pigments have a wide range of commercial applications in coating, printing, fluorescent labels for cells, antibodies, and DNA (Haugland, *Handbook of Fluorescent Probes and Research Products*, 9th Ed., Molecular Probes, Eugene, (2002); Seisenberger et al., *Sciences*, 294, 1929, (2001); Cotle et al., *J. Phys. Chem. B*, 105, 4999, (2001)). They are of particular interest because of their photosensitivity, color strength and overall stability. However, organic pigments are insoluble in water, and thus difficult to disperse in aqueous solution. Although there are a large variety of water soluble chromophores commercially available today, most of them exhibit relatively low fluorescence quantum yields and/or photochemical stabilities. Cyanine dyes, for example, are highly instable toward oxygen and light, while xanthenes dyes tend to aggregate in aqueous medium. The highly fluorescent perylene-3,4,9,10-tetracarboxdiimide chromophore is widely used as a commercial dye and pigment due to its outstanding chemical, thermal and photochemical stability (Nagao et al., *Dyes Pigm.*, 5, 171, (1984); Zollinger, *Color Chemistry* VCH, Weinheim, (1987); Christie, *Polym. Int.*, 34, 351, (1994)). Furthermore, because of it brilliant color, strong absorption, and fluorescence, it has been extensively investigated as an active compound in photovoltaic cells (Breeze et al., *Appl. Phys. Lett.*, 81, 3085, (2002)), light emitting diode (Kalinowski et al., *J. Appl. Phys.*, 83, 4242, (1998)), and light-harvesting complexes (Wurthner et al., *Org. Biomol. Chem.*, 1, 240, (2003)). Owing to the unique properties of these dyes, they should also be excellent biological probes; however, their solubility in aqueous medium is a critical issue.

BRIEF SUMMARY

Disclosed herein is a nanoparticle comprising: a surfactant shell having a hydrophilic outer surface and a hydrophobic inner surface; a polymer within the surfactant shell that comprises aromatic groups; and an organic chromophore within the surfactant shell.

Also disclosed herein is a method of making nanoparticles comprising: emulsifying an aqueous composition comprising a surfactant and an organic solution of a monomer and an organic chromophore to form micelles comprising the monomer and the chromophore inside a surfactant shell; and polymerizing the monomer.

Also disclosed herein is a compound having the structure below.

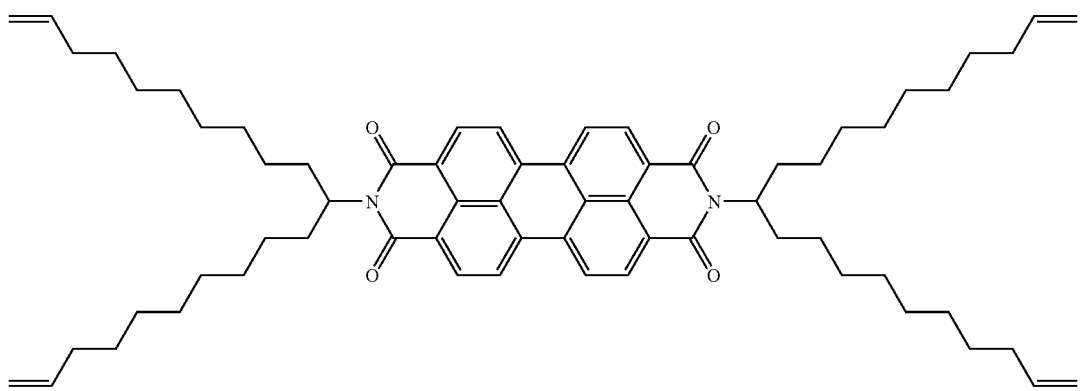 [SMILES: C=CCCCCCCCCC(CCCCCCCCC=C)N1C(=O)c2ccc3c4ccc5c6c(ccc(c7ccc(c2c37)C1=O)c64)C(=O)N(C(CCCCCCCCC=C)CCCCCCCCC=C)C5=O]

Also disclosed herein is a method comprising: reacting a ω-bromoalkyl acid with acryloyl acid lithium salt to produce an acryloyloxyalkyl carboxylic acid; and reacting the acryloyloxyalkyl carboxylic acid with sodium hydride to produce an acryloyloxyalkyl carboxylic acid sodium salt.

BRIEF DESCRIPTION OF THE DRAWINGS

A more complete appreciation of the invention will be readily obtained by reference to the following Description of the Example Embodiments and the accompanying drawings.

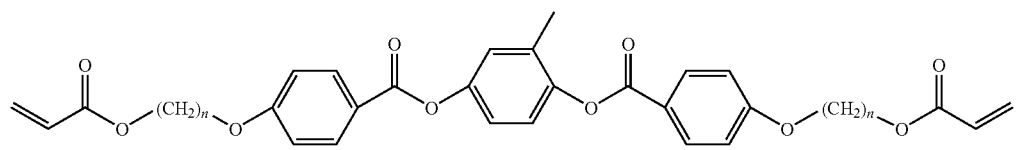

Figure 1:
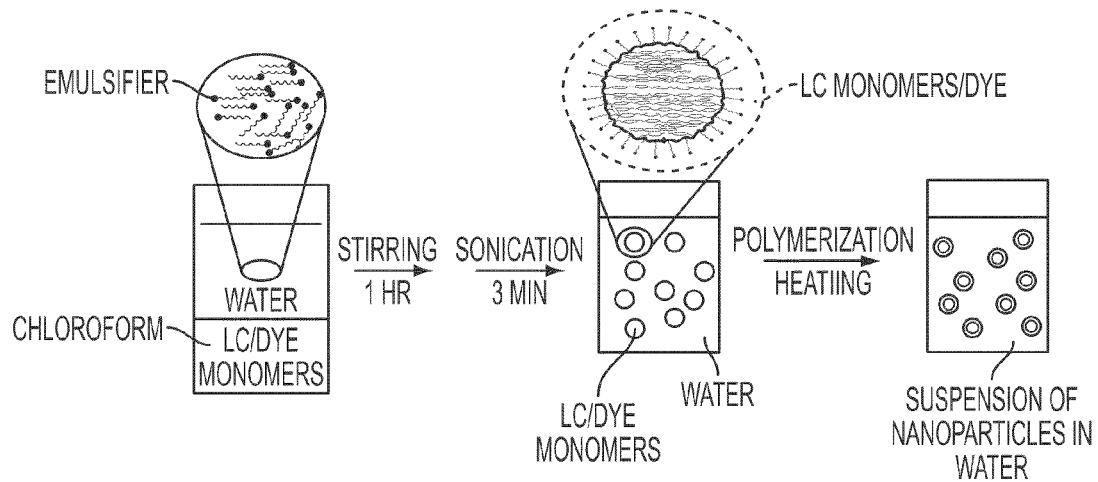
FIG. 1 shows a schematic representation of the miniemulsion process.
Figure 2:
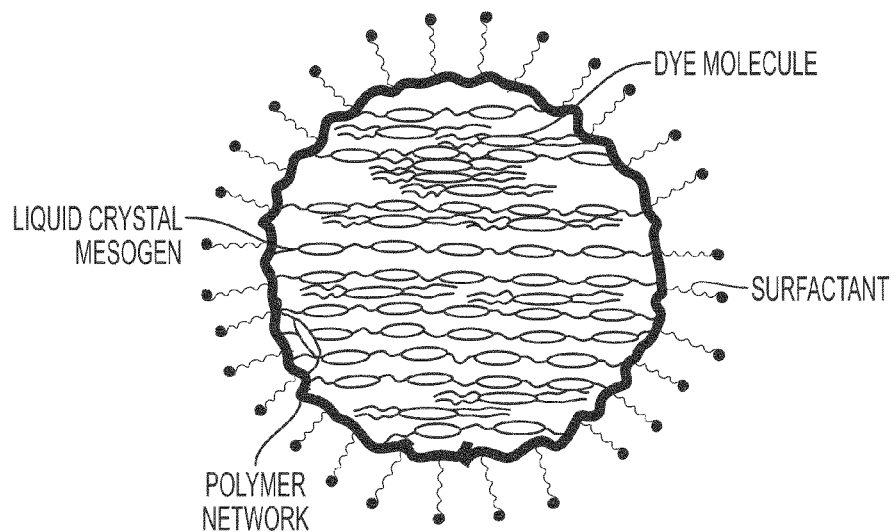
FIG. 2 shows a schematic representation of fluorescent liquid crystal nanoparticles.

Other suitable diacrylate monomers include, but are not limited to, hexamethyldiacrylate (HDA) and DABP11, shown below. These monomers can copolymerize with a surfactant to produce a nanoparticle, but may not show the tuning properties described below.

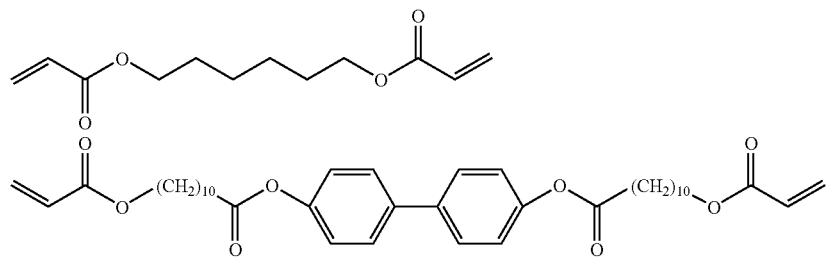

The chromophore is a compound that has fluorescent properties. The chromophore may be miscible with the polymer as an aid in tuning the fluorescence spectrum as described below. Suitable chromophores include, but are not limited to, perylenes and the perylene compound PERC11 shown below.

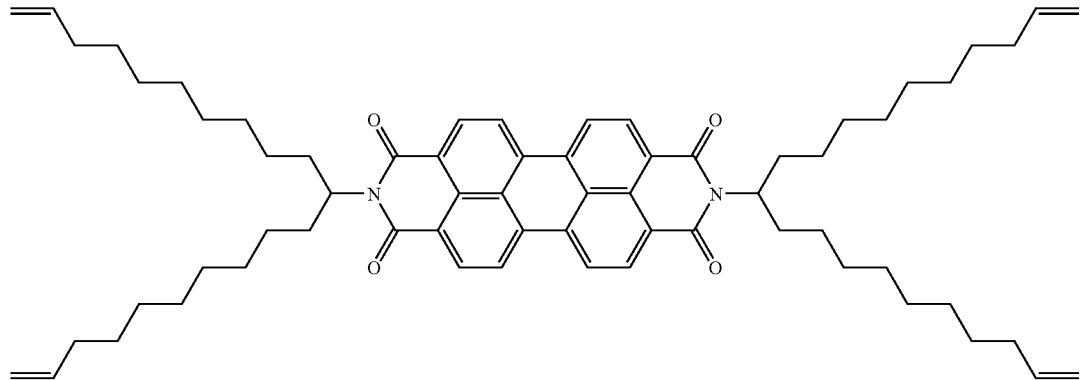 [SMILES: C=CCCCCCCCCC(CCCCCCCCC=C)N1C(=O)c2ccc3c4ccc5c6c(ccc(c7ccc(c2c37)C1=O)c64)C(=O)N(C(CCCCCCCCC=C)CCCCCCCCC=C)C5=O]

Although PERC11 has vinyl groups, it does not appreciably copolymerize or may not copolymerize at all with the monomer or surfactant because it lacks electron withdrawing groups adjacent to the vinyl groups. This makes polymerization of PERC11 highly disfavored compared to the other components.

PERC11 possesses two branched alkyl chains terminated by a vinyl group on either side of the molecule. The absorption and emission characteristics of PERC11 are not affected by the presence of the side chains at the N-imide position because of the nodes present at the imide nitrogen in both the HOMO and LUMO $\pi$-$\pi$ orbitals, which decouples the chromophore from the hydrocarbon chains. The side chains were chosen for two reasons. The first is that the conformational flexibility should lead to lower clearing points and enhance the solubility in organic solvents. Dyes with high melting points commonly exhibit low solubility in any medium because the crystal packing energy is too strong to be disrupted by exposure to solvents. Second, the increased density should allow the perylene aromatic cores to pack more tightly in order to maximize $\pi$-$\pi$ interactions. The absorption and emission characteristics of PERC11 are little affected by the presence of the side chains at the N-imide position because of the nodes present at the imide nitrogen in both the HOMO and LUMO $\pi$-orbitals. This can cause a decoupling of the chromophore from the hydrocarbon chains.

The substitution of the perylene aromatic core with vinylic branched chain leads to considerable lowering of the isotropization temperature to 60.7° C. The homologue material (Langhals et al., *J. Prakt. Chem.*, 333, 733, (1991)) without terminal vinyl groups has a melting point of 93.6° C. During cooling from the isotropic phase, optical textures were observed indicating the formation of mesophase in which the molecules are orthogonally arranged with respect to the stacking axis.

In some embodiments, the fluorescence spectrum may be tuned be adjusting the mole ratio of monomer to the chromophore. In this case the polymer contains LC or other aromatic groups that promote or interfere with the ability of the chromophore to self-aggregate. Miscibility of the chromophore with the polymer may assist in this process. In the case of PERC11 and DACTP11, when higher relative amounts of DACTP11 are present, it interferes with self-aggregation of the PERC11. The LC units tend to be inserted between the PERC11 molecules, resulting in green-shifted, monomeric-type fluorescence. When lower relative amounts of DACTP11 are present, the PERC11 forms larger aggregates, resulting in red-shifted aggregate-type fluorescence.

This process can be a method for generating multicolor luminescence from suspensions of liquid crystal/dye nanoparticles with a single wavelength excitation. By proper design of the LC network, one can have a direct control of the self-organization of dye molecules which in turn is responsible for the different emission of the nanoparticles. The nanoparticles can be prepared with sizes ranging from a few nanometers to a few hundred nanometers with good stability and biocompatibility. The invention provides wide ranges of potential applications such as multiplexed signaling, immunoassays, and bioassays.

The spectral and visual observations indicate control of PERC11 aggregation in fluorescent nanoparticles may be related to three parameters. The first is miscibility of the molecular species in the temperature range used to synthesize the nanocolloids. Immiscibility only promotes PERC11 aggregation during FNC synthesis. The second parameter is π-π molecular interactions between the components. HDA is miscible with PERC11 yet offers no control over the core interactions of PERC11. DABP11 exhibits a high order LC phase, but was not sufficiently miscible with PERC11 to provide the necessary π-π interactions to control dye aggregation. On the other hand, DACTP11 is a nematic material that is both miscible with PERC11 and has sufficient core interaction to segregate the dye and control aggregation. This would indicate that a liquid crystal component, specifically a molecule with the necessary core-core interactions with perylene, may play a role in controlling the aggregation of dye molecules. The third parameter is the ratio of the molecular species. By adjusting the amount of PERC11 from 0.6 mol % to nearly 5 mol % relative to DACTP11, the ability is demonstrated to carefully control the dye aggregation and tune the emission spectra of FNCs over a broad range of the visible spectrum. The nanoparticles can have useful fluorescent properties even without the tuning ability.

The process is not restricted to nanoparticles with one specific kind of cross-linkers and with carboxylic group based surfactants. Nanoparticles with surfactants terminated with imidazole, sulfonate or amine groups can be used. Cross-linker liquid crystal structures can be modified in order to show different mesophases such as smectic A for example. The dye molecule can be tailored in order to increase its solubility and stability. In addition, other dyes with good photostability could be confined within nanoparticles to vary the emission signature of the nanoparticles.

These nanoparticles may have advantages over currently available materials. The nanoparticles may be easily prepared, and the protein coated nanoparticles may be easily purified by centrifugation. The nanoparticles may provide a multivalent surface that facilitates measuring low affinity interactions. It can also provide an effective scaffold, permitting formation of multilayers.

The nanoparticles may be used in a number ways. In one method, a plurality of the nanoparticles is exposed to a sample suspected of containing one or more target molecules that bind to the outer surface of the nanoparticle. For example, an avidin may be bound to the nanoparticles, while the target may be bound to a biotin. After allowing time for any binding, the nanoparticles that are bound to the target molecules are isolated. Isolation involves separating any target-nanoparticle complexes from free nanoparticles. The fluorescence emission spectrum of any isolated nanoparticles is then measured. A fluorescence response can indicate the presence of the target.

The assay may use two or more different types of nanoparticles having different mole ratios of the chromophore to repeat units of the polymer, different fluorescence emission spectra, and different binding groups on the outer surface that bind to different target molecules. By this method two or more assays may be performed simultaneously. The assay may be designed such that there is a different fluorescence spectrum peak corresponding to each target to be detected.

In a variation of this embodiment, the target molecules may be found in biological cells. A after exposure and isolation of the nanoparticles, a fluorescence emission image of the cells will show what parts of the cells contain which targets. The effect is similar to staining the cells to visually show the locations of the various targets.

In another embodiment, the target molecules may be bound to microspheres, as in the Luminex system (Luminex Corp., Austin, Tex.).

The following examples are given to illustrate specific applications. These specific examples are not intended to limit the scope of the disclosure in this application. The techniques used may be generally applicable for other monomers, surfactants, and chromophores.

EXAMPLE 1

Synthesis of PERC11

Figure 3:
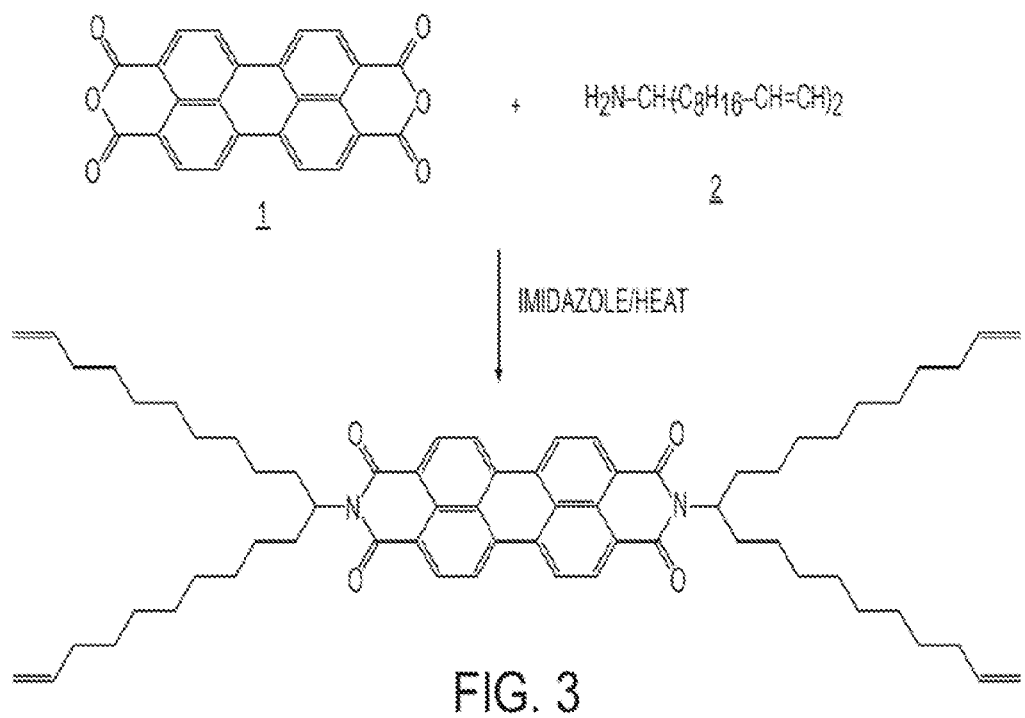
FIG. 3 shows a synthetic step for the synthesis of PERC11.

PERC11 was synthesized by condensation between perylene 1 amine 2 (FIG. 3). A typical procedure follows. In a 500 mL flask, 0.55 g (1.45 mmol) of perylene-3,4,10-tetracarboxylicdianhydride 1 and 1 g (3.25 mmol) of 1-dec-9-enyl-undec-10-enylamine 2 (Hopkins et al., *Macromolecules*, 36, 2206, (2003)) in 2.11 g imidazole were stirred for 6 hrs at 180° C. The reaction mixture was cooled down to room temperature and 15 mL of ethanol was added followed by 50 mL 2N HCl. The mixture was stirred overnight, the precipitate was filtered and washed thoroughly with water and dried overnight at 130° C. The material was further purified by silica gel column chromatography using an eluent mixture of dichloromethane/hexane 5/1 to yield a viscous material of approximately 80% yield. Classical characterization was performed using NMR and elemental analysis techniques.

EXAMPLE 2

Synthesis of Polymerizable Surfactant AC10COONa

Figure 4:
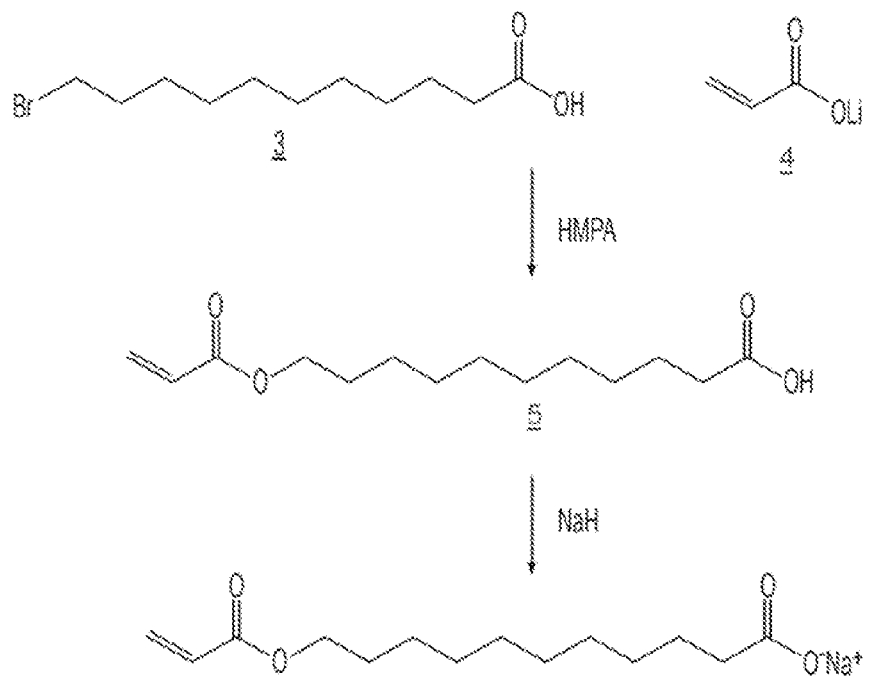
FIG. 4 shows the synthetic steps for the preparation of AC10COONa.

The reactive surfactant was synthesized following scheme shown in FIG. 4. 11-Bromo-undecanoic acid 3 was reacted with acryloyl acid lithium salt 4 to give the acrylate derivative 5. The salt of the acid 5 was prepared by dissolving it in THF solution of sodium hydride. A typical procedure is described.

A mixture of 3 2.13 g (8.04 mmol) and 4 0.85 g (8.04 mmol) in 25 mL of hexamethylphosphoramide (HMPA) was stirred overnight. Water was added, and the mixture was extracted from ether, washed with water and dried over $MgSO_4$. Silica gel column chromatography was performed in ethyl acetate/hexane to yield 1.5 g of white solid 5 (73% yield).

A solution of NaH 0.12 g (5 mmol) in 20 mL of THF was stirred in ice-bath under nitrogen. Then, a solution of 5 1.25 g (4.8 mmol) in THF was added dropwise. The mixture was further stirred for 30 min at room temperature. The solvent was evaporated under vacuum and the product AC10COONa obtained as a white powder was dried under vacuum: yield (100%).

EXAMPLE 3

Preparation of PER54 Liquid Crystal Miniemulsion

A mixture of DACTP11 (80 mg), PERC11 (5 mg), and AIBN initiator (5 mg) were dissolved in 3 g of chloroform and added to a solution of AC10COONa (15 mg) in 10 g of water. After stirring for 1 hr, the miniemulsion was prepared by ultrasonicating the mixture for 3 min at 90% amplitude with an ultrasonic processor (GEX-600). In order to remove the chloroform and to cross-link the liquid crystal and the surfactant, the sample was stirred for 6 hrs at 64° C. under nitrogen. The resulting nanoparticles were centrifuged and the supernatant was decanted and replaced with deionized water, and the sediment was redispersed. This centrifugation-redispersion cycle was repeated several times.

Several fluorescent nanoparticles samples with different initial dye concentrations were prepared. The miniemulsion process worked well with no precipitation occurring at the end of the reaction. The results, together with the size and polydispersity of the nanoparticles determined by light scattering are displayed in Table 1. The table shows that the miniemulsion leads to nanoparticles with approximately the same size regardless of the amount of dyes added. The polydispersity of the particles ranges from 0.029 to 0.005 confirms that the particles have a relatively uniform size.

TABLE 1

Nanoparticle sample and particle sizes.

| Sample | DACTP11 | PERC11 | AC10COONa | AIBN | Particle size | PDI | mol % PERC11 |
|---|---|---|---|---|---|---|---|
| PER54 | 80 mg | 2.5 mM | 15 mg | 5 mg | 208 nm | 0.015 | 4.8 |
| PER51 | 80 mg | 1.28 mM | 15 mg | 5 mg | 262 nm | 0.029 | 2.5 |
| PER64 | 80 mg | 0.8 mM | 15 mg | 5 mg | 201 nm | 0.022 | 1.5 |
| PER56 | 80 mg | 0.0084 mM | 15 mg | 5 mg | 237 nm | 0.005 | 0.02 |

(For each sample 10 g water and 2 g chloroform were used. The mol % PERC11 is relative to combined PERC11 and DACTP11.)

EXAMPLE 4

Particle Analysis

The size and the polydispersity of the LC nanoparticles were determined by dynamic light scattering at a fixed scattering angle of 90° using a Brookhaven Zeta Potential Analyzer. A scanning electron microscope (Carl Zeiss Supra 55) was used to collect images of nanoparticles deposited on an acid-cleaned silicon substrate. Silicon wafers were vertically pulled at slow speeds (0.25 μm/sec) from a diluted suspension of nanoparticles. Samples were dried and imaged to determine particle stability in dry conditions.

Figure 5:
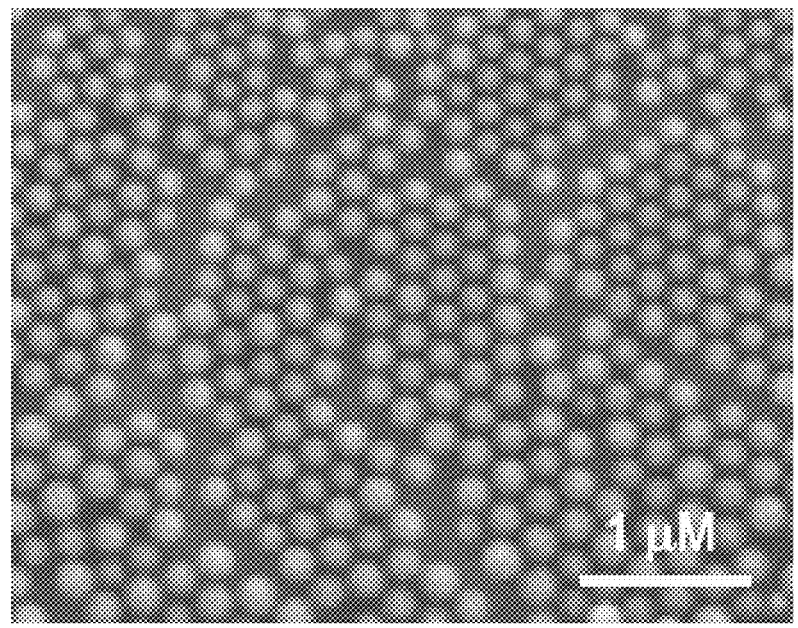
FIG. 5 shows an SEM photograph of example nanoparticles ordered on a silicon substrate.
Figure 6:
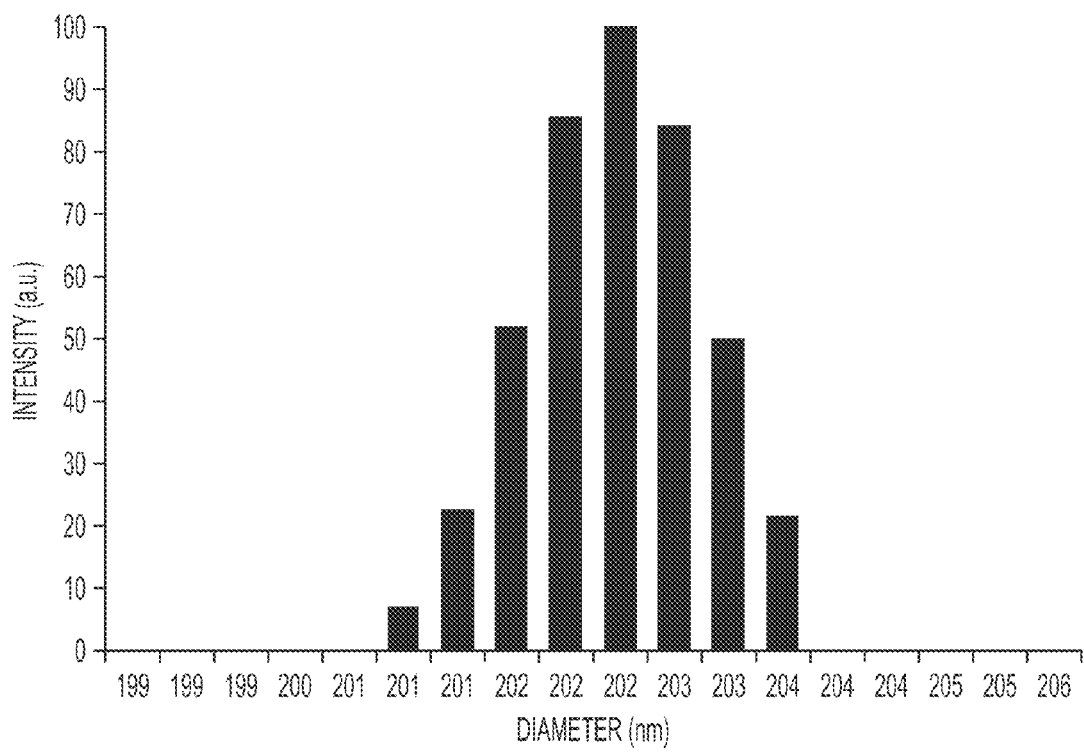
FIG. 6 shows diameter distribution of example nanoparticles as measured by light scattering in an aqueous suspension.

FIG. 5 shows a SEM photograph of PER52 (prepared with 0.3 mM PERC11) in which the nanoparticles display a good stability (no coalescence observed) and monodispersity. The stability of the particles is due to the quality of the surfactant and polymerization of the internal components. The surfactant has an acrylate end group which enhances the stability of the particles upon polymerization. FIG. 6 shows diameter distribution of PER52 as measured by light scattering in an aqueous suspension.

EXAMPLE 5

Spectral Characterization

UV-Vis spectra were performed on Carry 5000 UV-Vis spectrophotometer, and emission spectra were recorded on a FluoroMax-3 Spectrofluorometer at various concentrations of the dye. Spectra at all concentration were normalized to unity to emphasize the peak shapes. To record spectra at high concentrations, a thin quartz cell of 0.2 cm was used.

Figure 7:
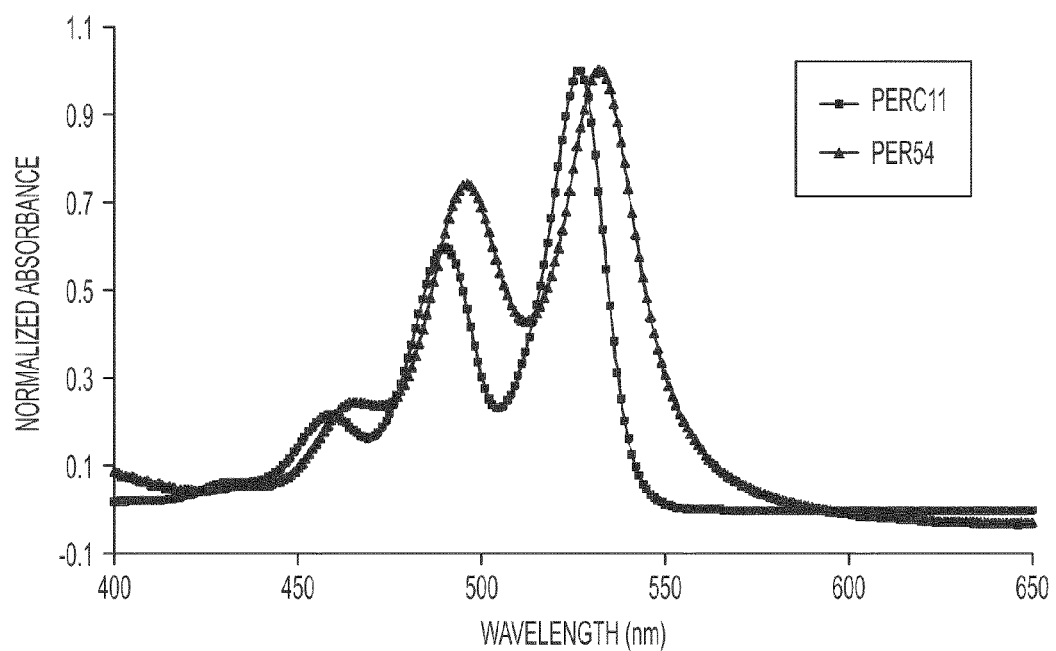
FIG. 7 shows UV-vis spectra of the dye PERC11 (12.5 µM) in chloroform and fluorescent nanocolloid (FNC) population PER54 (diluted to 10 µM in an aqueous suspension)

The absorption spectra of PERC11 in chloroform and fluorescent nanoparticles in water are shown in FIG. 7. The absorption spectrum of PERC11 shows three pronounced peaks (in the range of 445-540 nm) and a shoulder around 425 nm, which correspond to 0-0, 0-1, 0-2, and 0-3 electronic transitions, respectively. The spectrum of the nanoparticles looks similar to the PERC11 spectrum with a slight shift of the absorption peaks due to different environmental conditions surrounding PERC11 (chloroform vs. liquid crystal).

Figure 8:
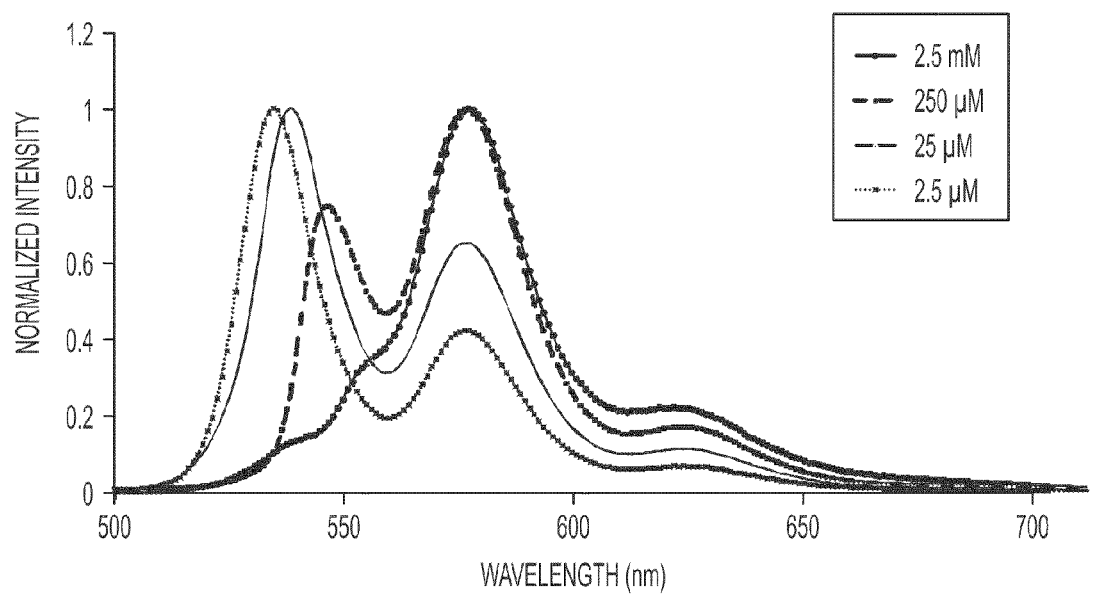
FIG. 8 shows emission spectra of PERC11 in chloroform at various initial concentrations excited at 487 nm

FIG. 8 shows the emission spectra of PERC11 excited at 487 nm in chloroform at various initial concentrations. In dilute concentrations (<2.5 μM), PERC11 exists predominately as free monomers with no self-organization (as evidenced by the green luminescence of the sample). When the initial concentration is high (>25 μM), intermolecular interactions increase and self-organization begins to take shape leading to orange and red luminescence colors.

Figure 9:
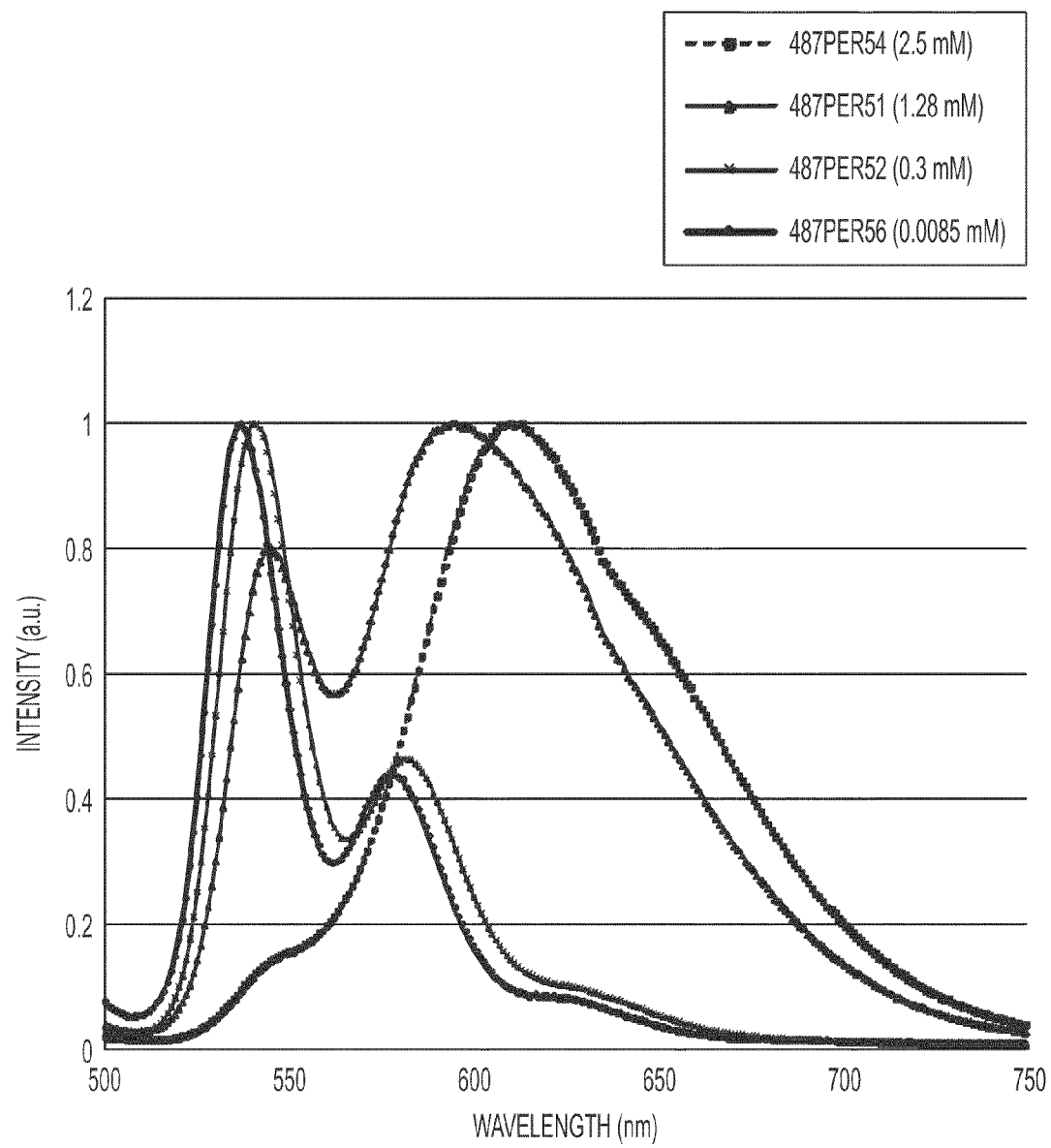
FIG. 9 shows fluorescence spectra of a series of nanoparticles at different concentrations in water excited at 487 nm.

The emission spectra of various nanoparticle suspensions (each containing a different initial concentration of PERC11) are shown in FIG. 9. Keeping the concentration of the liquid crystal (DACTP11) constant, we were able to tune the luminescence from green (nonaggregated monomers) to yellow, orange, and red upon aggregation.

Figure 10:
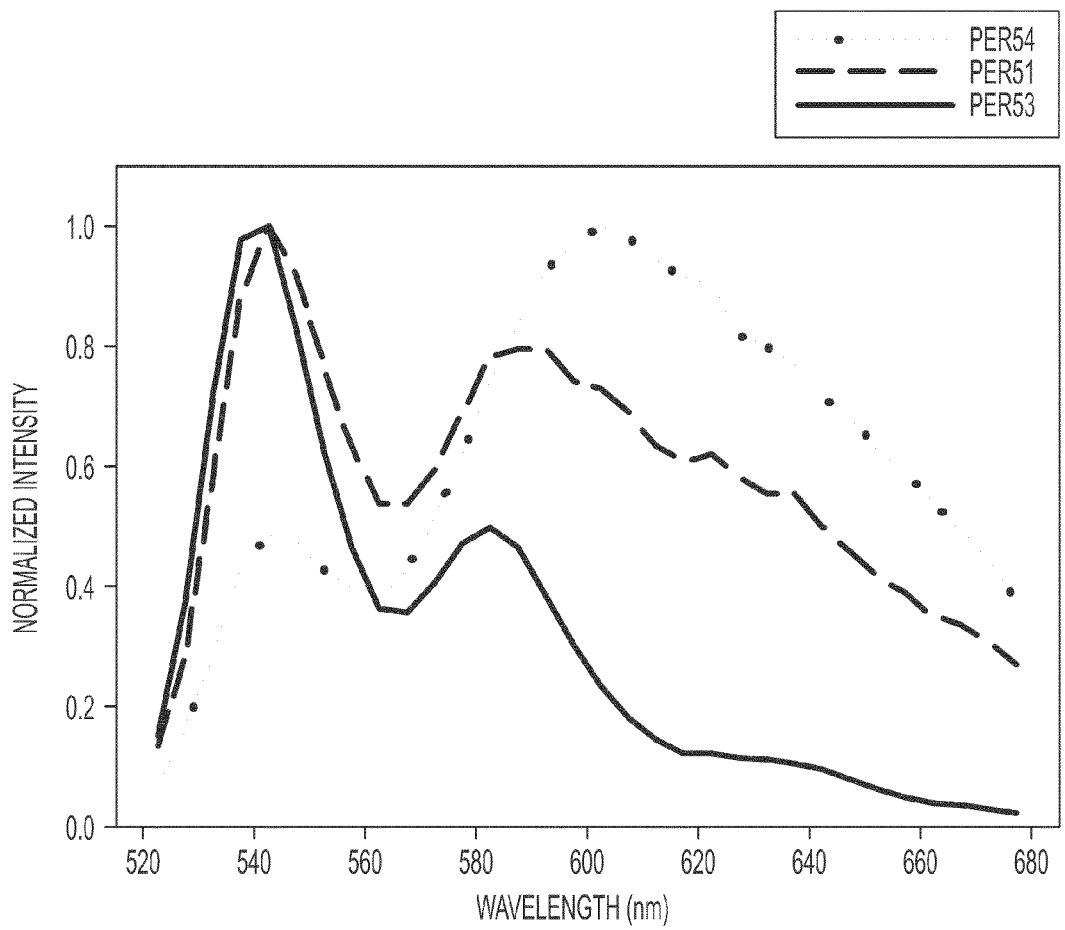
FIG. 10 shows emission spectra of three nanoparticle populations (red, orange, and green) when excited at 488 nm.
Figure 11:
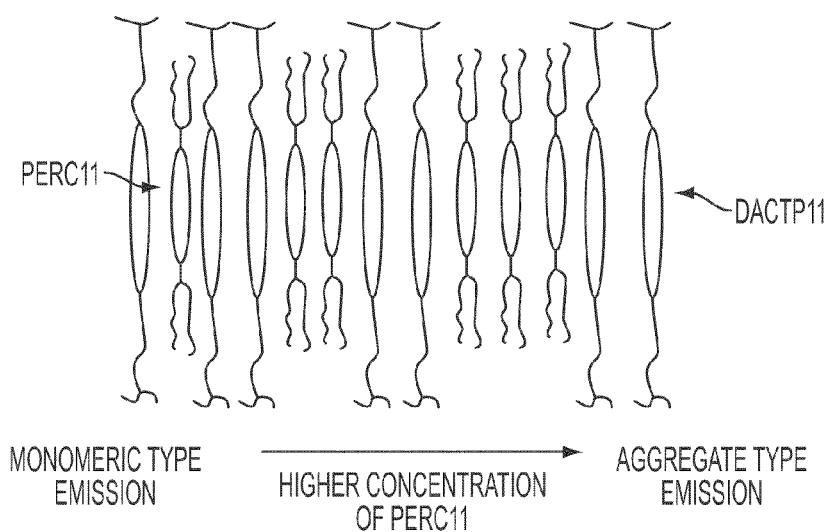
FIG. 11 shows a schematic representation of self-organized structures of PERC11/DACTP11 inside nanoparticles.

The tuned emission of different nanoparticle populations was also analyzed in a dry state by depositing the nanoparticles via vertical pulling of a silicon substrate from an aqueous suspension. Samples were imaged and the emission spectra collected with a spectral image confocal microscope system (Nikon C1-si, Nikon Corp.). As shown in FIG. 10, the emission spectra of different populations vary significantly, thus confirming the stability of the monomeric and/or aggregated dye molecules within the nanoparticles. Direct collaboration of the liquid crystals may influence this tunable behavior. For high initial concentration of PERC11 (2.5 mM, PER54), there was no emission detected from individual molecules (free monomers). This result implies that all the dye molecules were assembled into aggregate because of the inability of LC molecules to separate their assemblies, i.e. π-π stacking of PERC11 molecules is much stronger that the LC-PERC11 interaction. This leads to a significant red shift emission ($\lambda_{max}$~610 nm) measured for the aggregate phase. Such an eximer-like state is usually weakly emitting for aggregate with strong π-π stacking as observed for molecules with linear side chains (Balakrishnan et al., *J. Am. Chem. Soc.*, 127, 10496 (2005)). The high fluorescence observed for PER54 assembly is likely due to the distorted molecular packing caused by the branched side chains. Such behavior has been observed for similar distorted molecules. Continuously decreasing the initial concentrations of PERC11 from 2.5 mM to 8.4 µM led to a gradual transformation of aggregate to free molecules. This behavior can be explained by the strong π-π interactions between PERC11 and liquid crystal DACTP11 molecules as the concentration of the dye is getting smaller. As shown in FIG. 11, the ability of DACTP11 to control self-organization of dye molecules increases with decreasing PERC11 concentrations.

Figure 12:
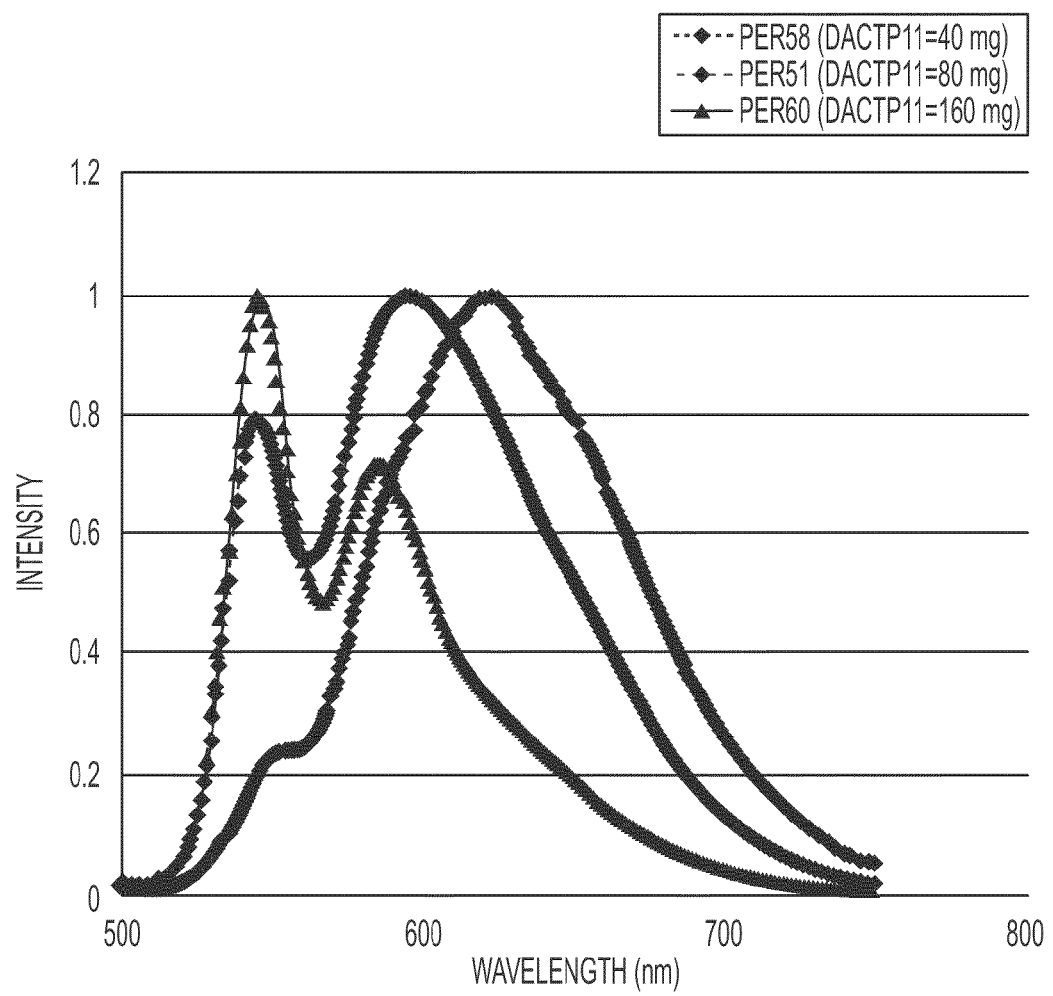
FIG. 12 shows emission spectra of nanoparticles in water at different concentrations of PERC11. Excitation wavelength at 487 nm.

To demonstrate the effect of liquid crystal DACTP11 on the self-organization of dye molecules, a control experiment was performed consisting of changing the concentration of DACTP11 inside the nanoparticles and keeping constant the initial amount of PERC11 (and all other components). An example for this experiment is shown in FIG. 12. At low concentration of DACTP11 (PER58), PERC11 molecules undergo aggregation due to low interaction with the liquid crystal molecules. As a result, a new red-shifted emission emerges at 620 nm. Increasing the concentration of DACTP11 (PER58) leads a green-shifted emission ($\lambda_{max}$=545 nm) from the nanoparticles. This implies that in the presence of elevated levels of DACTP11 the dye molecules exist predominately in monomeric forms. This control experiment demonstrates that the liquid crystal molecules play a crucial role in controlling the aggregation of dye molecules.

Figure 13:
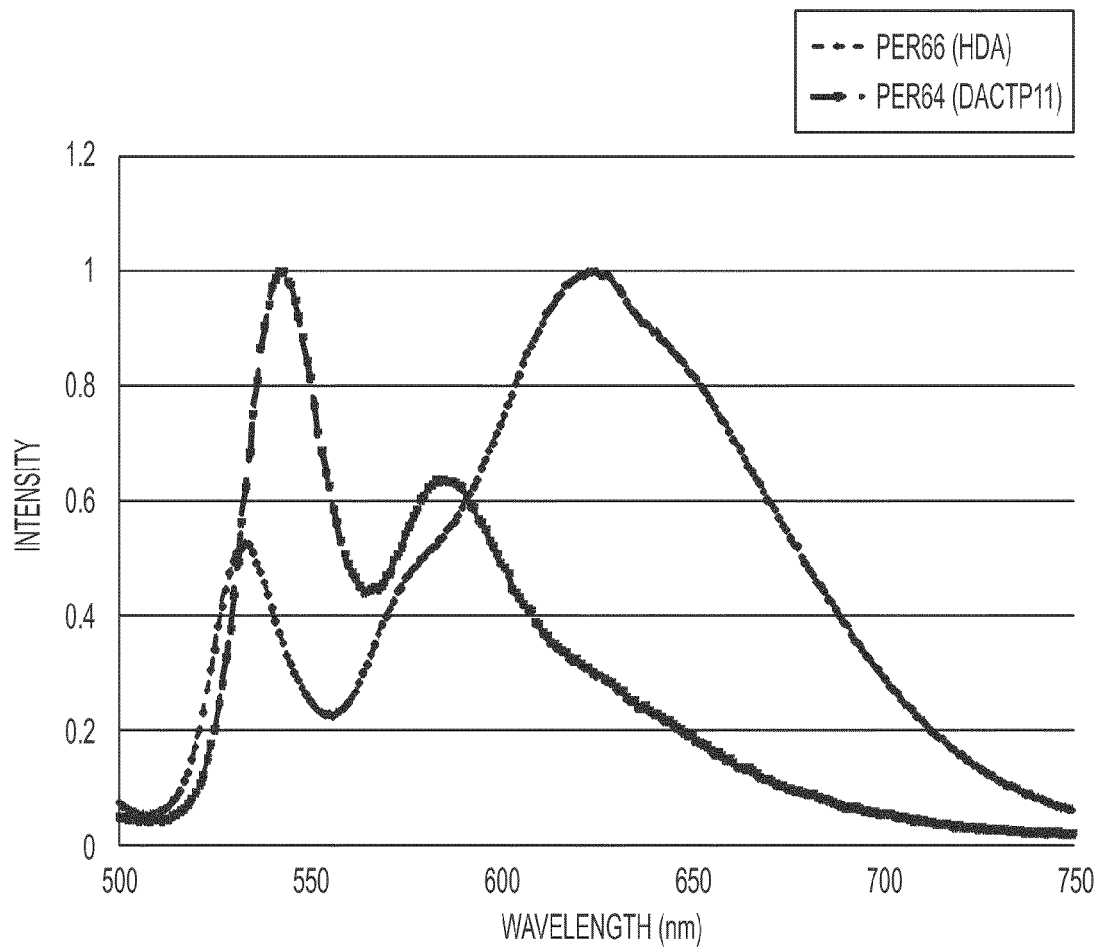
FIG. 13 shows a comparison of emission spectra of PER64 and PER66 in water at 487 nm.

In a second control experiment, DACTP11 was replaced by HDA (1,6-hexamethylene diacrylate). HDA is a cross-linker consisting of a six carbon alkane chain terminated by two acrylate groups. HDA is a flexible molecule and lack the rigidity exhibited by DACTP11 and therefore, no π-π interactions between PERC11 and HDA molecules would be expected within the nanoparticle. PER64 was chosen as a reference sample that shows a fluorescence emission in the yellow range of the spectrum. A new sample PER66 consisting of HDA as the cross-linker and keeping the initial concentration of PERC11 the same (0.8 mM) as in PER64 sample was prepared. The fluorescence of PER66 in water is shown in FIG. 13. A significant red-shifted emission of the nanoparticle sample was observed. This implies that all the dye molecules were assembled into aggregate due to the non-existent π-π interaction between PERC11 and HDA molecules. This experiment further demonstrates that DACTP11 is in part responsible for the molecular organization of the dye molecules within the nanoparticles.

EXAMPLE 6

Bioconjugation of Proteins to Nanoparticles and Use as Tracers in Immunoassays

Due to the many available carboxyl groups on the surface of the nanoparticles, bioconjugation of proteins may be done by the straightforward application of known protein crosslinking methodologies. In the following example a water soluble carbodiimide (1-ethyl-3-(3-dimethylaminopropyl)carbodiimide hydrochloride, EDC) is utilized to activate the nanoparticles' carboxyl residues. These activated groups are stabilized by the formation of an intermediate in the presence of sulfo-NHS (N-hydroxysulfosuccinimide). The nanoparticles (PER51) are dialyzed at pH 6.0 for one hour to allow for complete activation of the surface carboxyls and removal of excess reactants and reaction byproducts. Then the protein to be conjugated to the nanoparticle surface is added and the nanoparticles dialyzed in a solution of higher pH (i.e. phosphate buffered saline at pH 7.4), to complete the covalent linking of the nanoparticles carboxyl groups to available amines found on the protein, primarily lysines. In the example shown, the biotin binding protein, NeutrAvidin (NA), is used. However this same chemistry could be utilized for any protein such as antibodies, lectins, or peptides, or any other bonding ligand. Once the conjugation was complete any unbound protein is easily removed by centrifugation of the nanoparticles.

Figure 14:
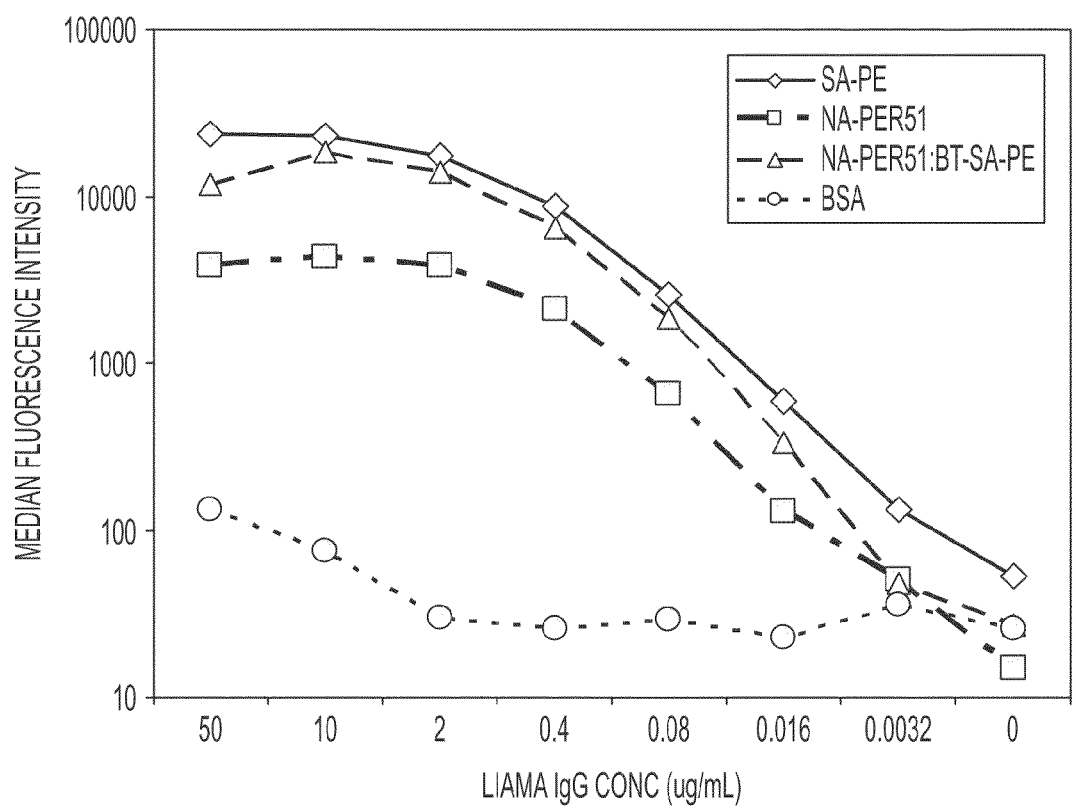
FIG. 14 shows a titer of llama anti-ricin antibody.

These NA-nanoparticle can then be used as efficient multivalent fluorescent tracers in immunoassays. As shown in FIG. 14, the NA-nanoparticles were compared to the current industry standard, a conjugate of streptavidin and phycoerythrin (SA-PE). In an experiment to evaluate the amount of antigen specific antibody in a polyclonal preparation, dilutions of the llama anti-ricin IgG were added to Luminex microspheres which had been coupled with ricin. After 30 minutes, the unbound antibody was filtered away, and a biotinylated goat anti-llama IgG (5 µg/mL) was added to each sample. After 30 additional minutes, any unbound goat anti-Llama IgG was filtered away, the microspheres washed once, and then either SA-PE or NA-PER51 was added to the Luminex microsphere and allowed to bind for 30 minutes. Afterwards, unbound material was filtered away, the microsphere resuspended in wash buffer and then measured by the Luminex flow analyzer. While the SA-PE provides the largest signal, in part due to the fact the current instrumentation is designed to be optimal for PE, the NA-PER51 provides a strong fluorescent signal as well, and has the same limit of detection as SA-PE. A second set of NA-PER51 was further amplified by addition of biotinylated-PE, which shows the availability of additional NA on the bound NA-PER51. Of note, NA-PER51 has a very low background that was generated at the lowest concentrations tested, providing sensitivity equal to SA-PE. Furthermore, the signal could be amplified by addition of Biotinylated-PE which bound to additional NA on the nanoparticle surface.

FIG. 14 shows the effectiveness of the NeutrAvidin conjugated PER51 nanoparticles in an immunoassay. It compares well to standard tracer streptavidin-phycoerythrin. In addition, it can be amplified by addition of biotinylated-phycoerythrin. Importantly, the nonspecific background binding is very low. The top three curves show ricin coated Luminex microspheres while the bottom curve is a control set of microspheres coated with bovine serum albumin (BSA).

Figure 15:
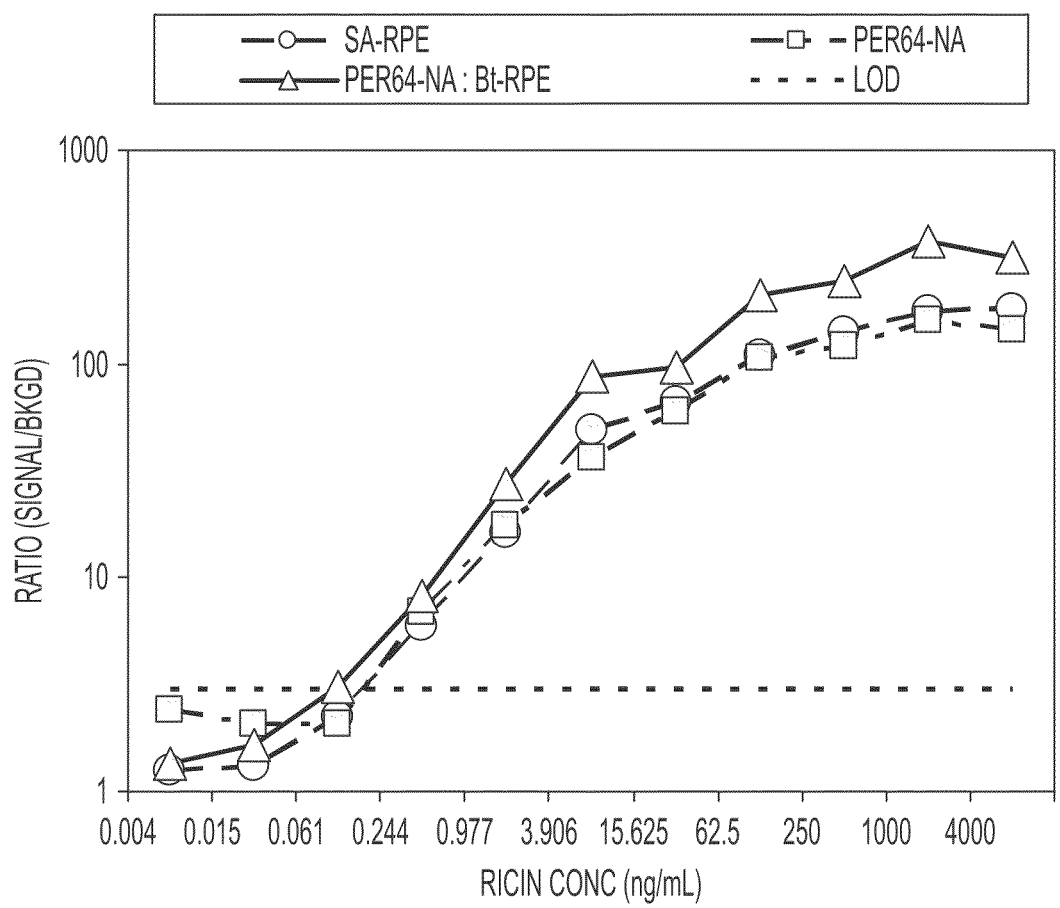
FIG. 15 shows a sandwich fluoroimmunoassay for ricin on the Luminex flow analyzer using various tracers with the same capture antibody and biotinylated antibody pair.

Following these initial experiments, NeutrAvidin coated PER64 nanospheres were prepared which more closely match the excitation and emission requirements of the Luminex flow cytometer. Using these PER64-NA nanospheres as the tracer in a sandwich fluoroimmunoassay for ricin, it was found that they were equal to standard streptavidin-phycoerythrin (FIG. 15). PER64-NA did as well as SA-RPE, and when the PER64-NA was amplified by Bt-RPE the signal doubled, but more importantly it gave a better signal to noise ratio, improving the limit of detection by a factor of 4, not seen previously using SABS amplification (Anderson et al., *Sensor Lett.*, 6, 213, (2008)). Of significance, when an additional fluorescent layer of biotinylated phycoerythrin was added to these nanospheres, the signal level increased by approximately 100%, and the limit of detection was improved as well. These experiments show that these nanospheres are already showing promising results for use as tracer reagents in fluoroimmunoassays.

EXAMPLE 7

HDA and DABP11 Monomers

Figure 16:
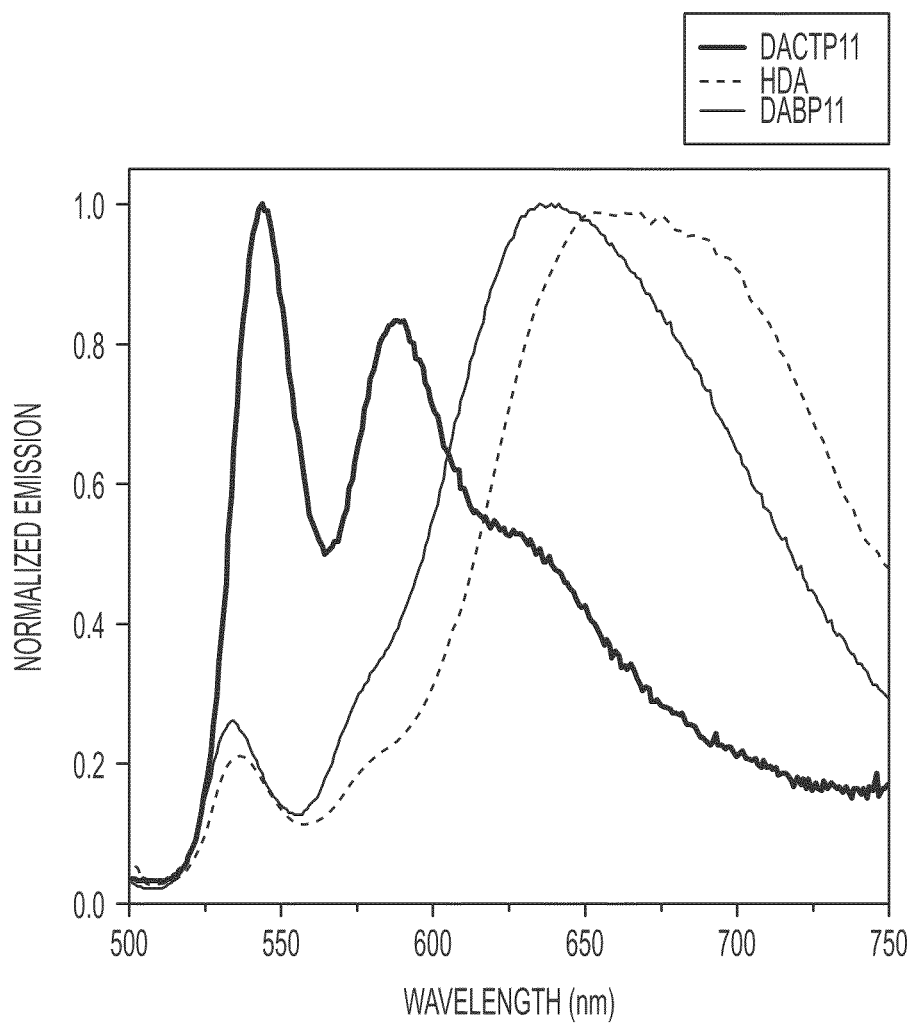
FIG. 16 shows emission spectra of F crosslinking, mesogenic monomer below where n is 11, known as DACTP11. The value of n may also be 8, 9, 10, or 12. DACTP11 shows a stable liquid crystal mesophase with the following transition: K 78.7 N 102.5 Iso.

Nanoparticles were made with DACTP11 replaced by two alternative diacrylates, hexamethyldiacrylate (HDA) and DABP11. HDA consists of a six carbon alkane chain terminated by two acrylate groups and is not expected to have any $\pi$-$\pi$ interactions with PERC11. On the other hand, DABP11 is a highly crystalline molecule with two phenyl rings at its core. Using an FNC sample with a yellow fluorescence emission as a reference sample (1.6 mol % PERC11), two samples containing the same mole percent of either HDA or DABP11 were prepared with the same mole percent PERC11. As shown in FIG. 16, the fluorescence of the two control samples compared to the yellow FNC spectrum show a severely redshifted emission, indicating PERC11 aggregation. As expected, the sample containing HDA is unable to control the dye aggregation due to the non-existent $\pi$-$\pi$ interaction with perylene. However, the emission of the sample prepared with DABP11 was not expected since DABP11 has a molecular core and was expected to have some $\pi$-$\pi$ molecular orbital interaction with PERC11.

Bulk contact preparations of DABP11 and PERC11 demonstrate that these two components have low miscibility with limited mixing at the contact line. In comparison, bulk contact preparations with PERC11 and DACTP11 readily mixed leading to a relatively diffuse interface between the two components when DACTP11 was in the nematic phase.

EXAMPLE 8

Bulk Contact Preparations of PERC11 and Cross-Linking Agents

The miscibility of PERC11 with the two cross-linking agents DACTP11 and DABP11 was examined using a classic contact technique on a Linkam hot stage (Linkam Scientific Instruments, Tadworth, UK) mounted on a polarized light microscope. Cross-linking agent was drawn under a glass coverslip on a microscope slide by capillary action as the sample was heated to the isotropic phase. When a significant portion of the coverslip area was filled with the cross-linking agent, the sample was cooled and excess material removed. On the opposite side of the coverslip, PERC11 was drawn under the coverslip in a similar manner. As the PERC11 approached the cross-linking agent, the temperature of the microscope slide was adjusted so that DACTP11 or DABP11 was either in an LC or isotropic phase. The mixing at the contact line was then observed to determine how miscible the two components were with one another.

On the one hand, when PERC11 is brought into contact with DABP11 there is very limited mixing and a rather unusual behavior is observed. When the two components contact one another with DABP11 showing a high order LC phase (T=85° C.), there is no visible mixing at the interface. This indicates the materials have a low miscibility. When PERC11 is brought into contact with DACTP11 in the nematic phase (T=100° C.), a relatively diffuse contact line rapidly develops. As the two components mix and the sample is cooled to 70° C., a liquid crystalline phase begins to appear in regions with a high concentration of PERC11, despite the fact that the transition temperature to the isotropic phase of pure PERC11 is 68° C. This observation is an indication of DACTP11 mixing well with PERC11 since the phase behavior at the mixture interface has been altered with respect to the pure materials. In general, the contact preparations of PERC11 with either DACTP11 or DABP11 demonstrate that miscibility of the components with one another is a primary factor that controls the dye aggregation in FNCs synthesized with DACTP11.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:
1. A composition comprising:
a plurality of nanoparticles, each nanoparticle comprising:
a surfactant shell having a hydrophilic outer surface and a hydrophobic inner surface made from a surfactant having an acrylate group;
a polymer within the surfactant shell made from a monomer having two or more acrylate groups, and that comprises liquid crystalline groups having $\pi$ molecular orbitals; and
an organic chromophore having the formula

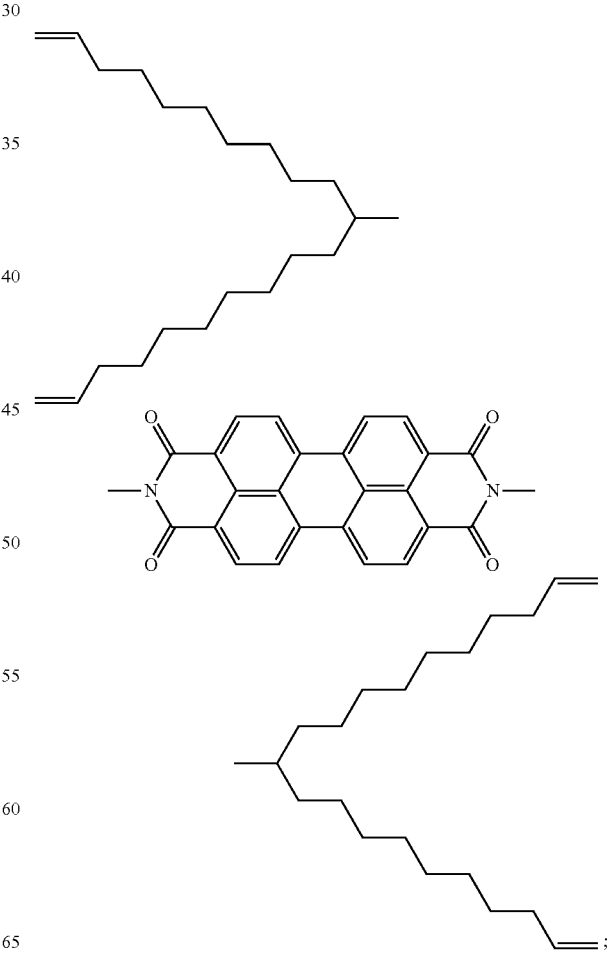

wherein the composition comprises two or more different types of nanoparticles having the same chromophore and polymer;
wherein the chromophore is not appreciably copolymerized with the monomer or surfactant; and
wherein the different types of nanoparticles have different mole ratios of the chromophore to repeat units of the polymer, different fluorescence emission spectra peaks, and different binding groups on the outer surface that bind to different target molecules.

2. The composition of claim 1, wherein the polymer is crosslinked.

3. The composition of claim 1, wherein the monomer has the formula:

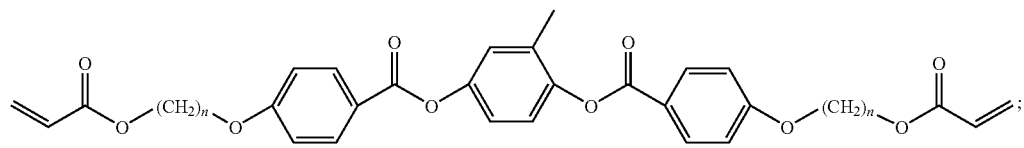

wherein n is an integer from 8-12.

4. The composition of claim 3, wherein n is 11.

5. The composition of claim 1, wherein the surfactant is copolymerized with the polymer.

6. The composition of claim 5, wherein the surfactant has the formula:

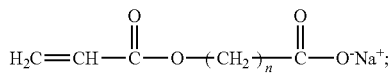

wherein n is an integer from 6 to 14.

7. The composition of claim 5, wherein the surfactant has the formula:

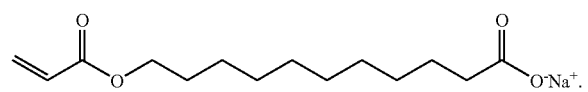

8. The composition of claim 1, wherein the outer surface of the surfactant shell comprises carboxylic groups that are coupled to biomolecules.

9. The composition of claim 1, wherein the composition is an aqueous suspension of the nanoparticles.

10. A method comprising:
exposing the composition of claim 1 to a sample suspected of containing one or more target molecules that bind to the outer surface;
isolating any nanoparticles that are bound to the target molecules; and
measuring the fluorescence emission spectrum of the isolated nanoparticles.

11. The method of claim 10, wherein the sample comprises a plurality of microspheres suspected of having the target molecules bound thereto.

12. A method comprising:
exposing one or more cells to the composition of claim 1; and
producing a fluorescence emission image of the cells.

13. A method of making the composition of claim 1 comprising:
emulsifying an aqueous composition comprising a surfactant having an acrylate group and an organic solution of a monomer having two or more acrylate groups and an organic chromophore having a first molar ratio to form micelles comprising the monomer and the chromophore inside a surfactant shell;
wherein the chromophore has the formula:

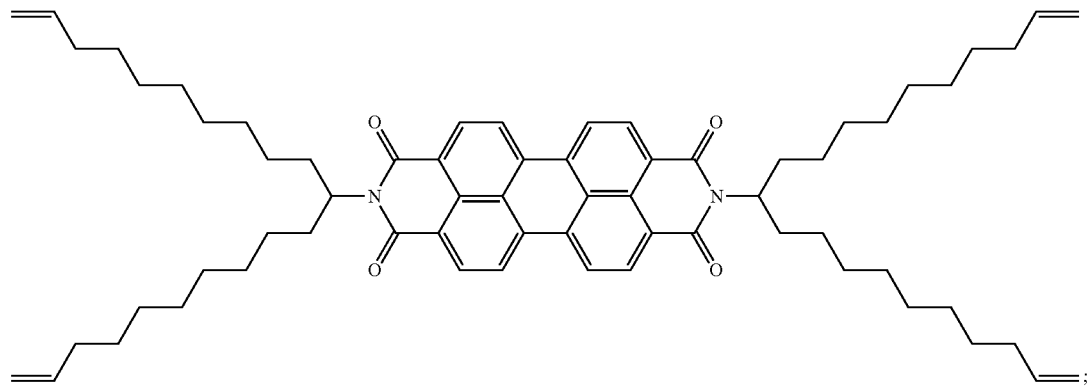 [SMILES: C=CCCCCCCCCC(CCCCCCCCC=C)N1C(=O)c2ccc3c4ccc5c6c(ccc(c7ccc(c2c37)C1=O)c64)C(=O)N(C(CCCCCCCCC=C)CCCCCCCCC=C)C5=O]

polymerizing the monomer to form a first plurality of nanoparticles comprising a polymer that comprises liquid crystalline groups having π molecular orbitals;
adding a binding group to the outer surface;
repeating the emulsifying, polymerizing, and adding with the monomer and the chromophore having a second molar ratio to form a second plurality of nanoparticles; and
combining the first plurality of nanoparticles and the second plurality of nanoparticles to form a composition comprising two or more different types of nanoparticles having the same chromophore and polymer;
wherein the chromophore is not appreciably copolymerized with the monomer or surfactant; and
wherein the different types of nanoparticles have different mole ratios of the chromophore to repeat units of the polymer, different fluorescence emission spectra peaks, and different binding groups on the outer surface that bind to different target molecules.

14. The method of claim 13, further comprising: removing the organic solvent.

15. A compound having the formula:

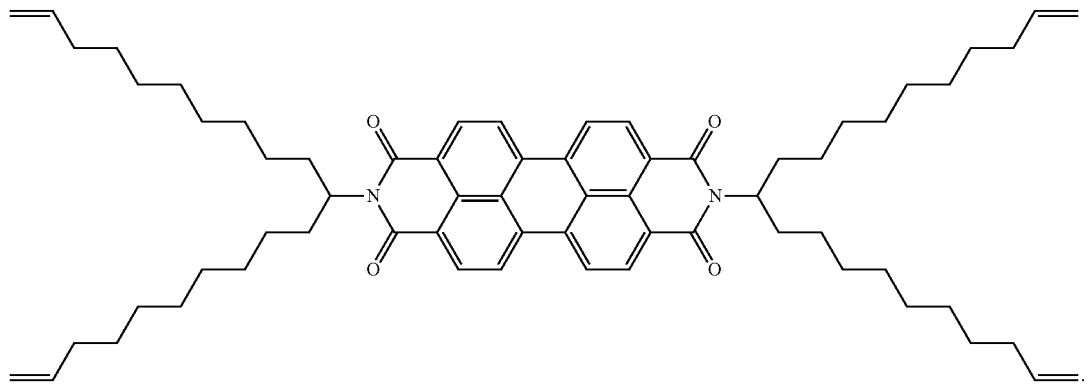 [SMILES: C=CCCCCCCCCC(CCCCCCCCC=C)N1C(=O)c2ccc3c4ccc5c6c(ccc(c7ccc(c2c37)C1=O)c64)C(=O)N(C(CCCCCCCCC=C)CCCCCCCCC=C)C5=O]

* * * * *